United States Patent
Seitz et al.

(10) Patent No.: US 7,958,922 B2
(45) Date of Patent: Jun. 14, 2011

(54) THERMO-ENCAPSULATING APPARATUS FOR PROVIDING A SEPARATOR ENVELOPING AN ELECTRODE OF AN ELECTRICAL ENERGY STORAGE DEVICE

(75) Inventors: Keith W. Seitz, Clarence Center, NY (US); Steven Schmit, Lockport, NY (US); Shawn Patterson, Buffalo, NY (US); Laurie O'Connor, East Aurora, NY (US)

(73) Assignee: Greatbatch Ltd., Clarence, NY (US)

( * ) Notice: Subject to any disclaimer, the term of this patent is extended or adjusted under 35 U.S.C. 154(b) by 962 days.

(21) Appl. No.: 11/951,601

(22) Filed: Dec. 6, 2007

(65) Prior Publication Data

US 2008/0236731 A1    Oct. 2, 2008

Related U.S. Application Data

(60) Provisional application No. 60/888,179, filed on Feb. 5, 2007.

(51) Int. Cl.
*B32B 37/06* (2006.01)
*B32B 38/04* (2006.01)
*B30B 5/00* (2006.01)

(52) U.S. Cl. .......... 156/515; 156/581; 156/583.4
(58) Field of Classification Search .......... None
See application file for complete search history.

(56) References Cited

U.S. PATENT DOCUMENTS

| | | | |
|---|---|---|---|
| 2,765,394 A * | 10/1956 | Griffith | 219/69.15 |
| 3,190,051 A * | 6/1965 | Souligney | 53/471 |
| 3,347,733 A * | 10/1967 | Elver | 156/515 |
| 3,354,605 A * | 11/1967 | Amberg et al. | 53/412 |
| 3,452,513 A * | 7/1969 | Owens, Jr. | 53/329.3 |
| 6,092,578 A * | 7/2000 | Machida et al. | 156/358 |
| 6,508,901 B2 | 1/2003 | Miller et al. | |
| 7,204,069 B2 * | 4/2007 | Liao | 53/510 |

* cited by examiner

*Primary Examiner* — Kat Wyrozebski
*Assistant Examiner* — Barbara J. Musser
(74) *Attorney, Agent, or Firm* — Michael F. Scalise

(57) ABSTRACT

An apparatus and method for cutting and heat sealing separator materials enveloping individually shaped electrode is described. The electrodes can be cathodes, anodes or other active components for incorporation into batteries, capacitors, and other implantable medical devices.

31 Claims, 17 Drawing Sheets

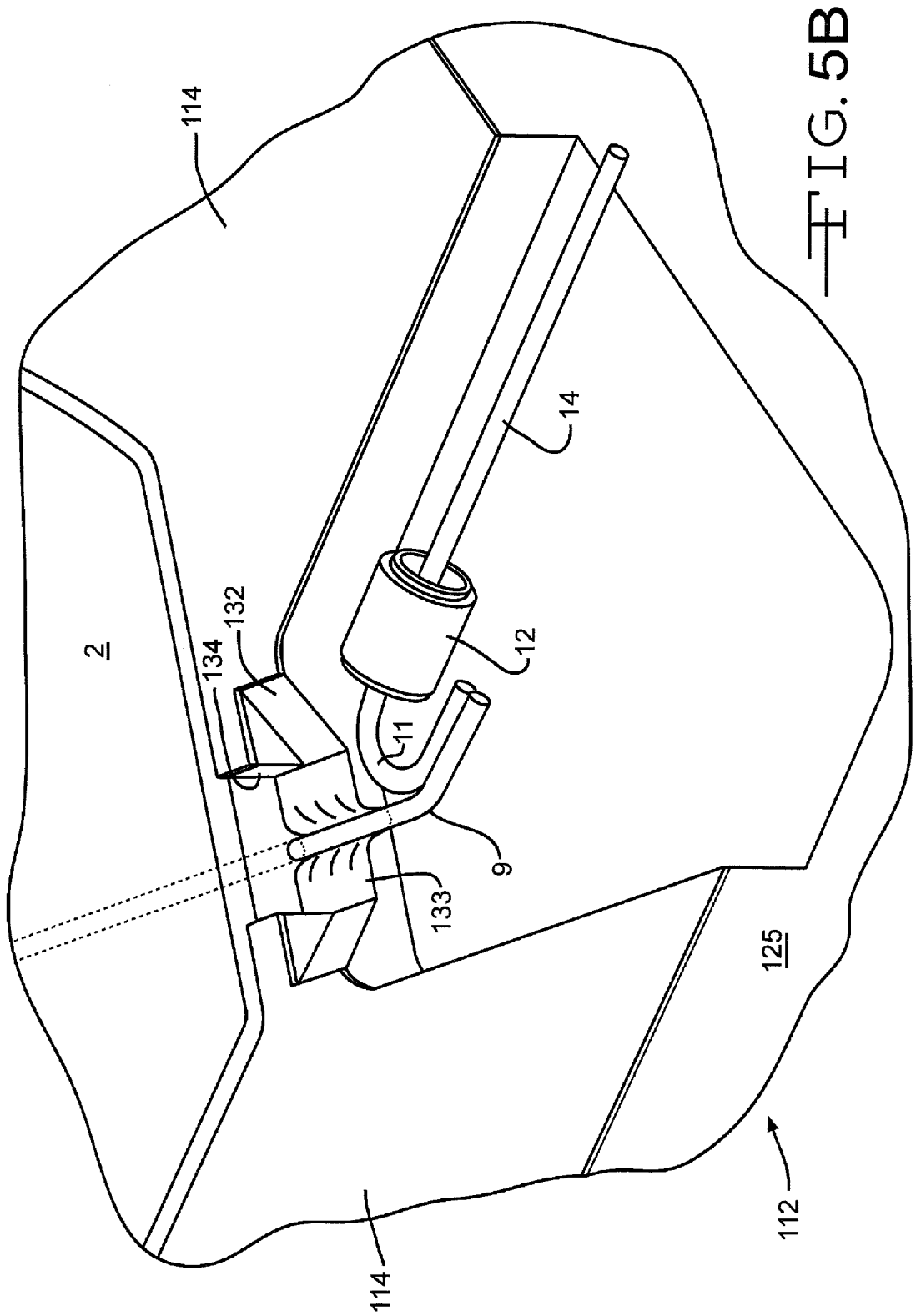

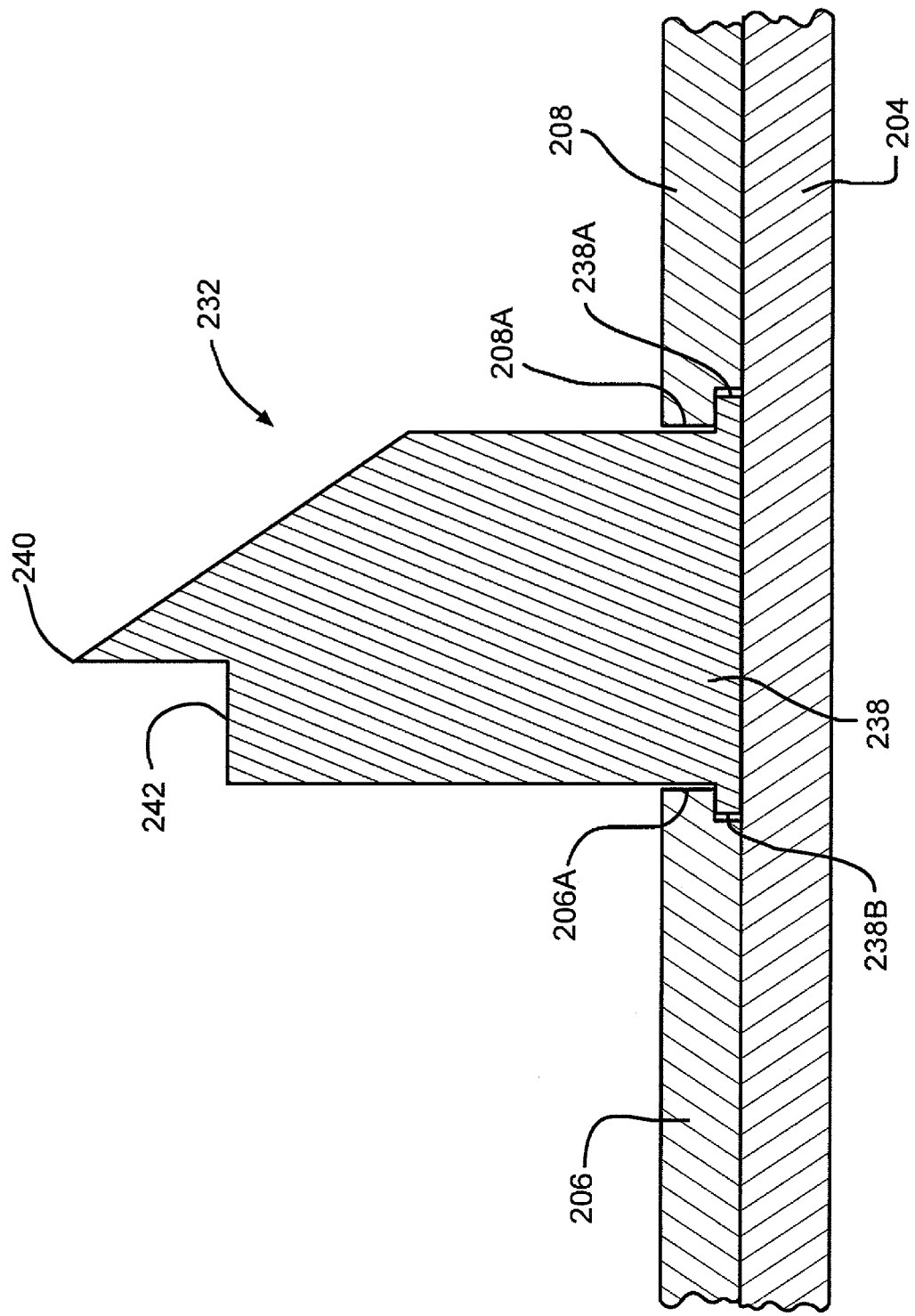

THERMO-ENCAPSULATING APPARATUS FOR PROVIDING A SEPARATOR ENVELOPING AN ELECTRODE OF AN ELECTRICAL ENERGY STORAGE DEVICE

CROSS-REFERENCE TO RELATED APPLICATION

This application claims priority from U.S. provisional application Ser. No. 60/888,179, filed Feb. 5, 2007.

BACKGROUND OF THE INVENTION

1. Field of the Invention

The present invention pertains generally to an apparatus and method for manufacturing components for implantable medical devices such as batteries or capacitors. More particularly, the present invention relates in one embodiment to thermal encapsulation of a battery or capacitor electrode within a protective polymer film.

2. Description of Related Art

Devices for heat sealing a variety of objects within thermoplastic films are generally known. Additionally, the sealing of capacitor and battery electrodes within thermoplastic films is also known. The encapsulation of an electrode within a porous polymer film is also known. The film provides a physical separation between the electrode, and an associated opposite polarity electrode, thereby preventing a short circuit between the electrodes.

Conventional thermal encapsulation systems generally are capable of cutting and sealing low melting point thermoplastic polymers such as polypropylene, but are not effective at processing polytetrafluoroethylene (PTFE) and similar high melting temperature fluoropolymers. However, subsequent capacitor or battery manufacturing processes after electrode encapsulation, such as case welding, occur at high temperatures. Low melting polymer separator films can be damaged during these processes, resulting in product that must be scrapped. Additionally, the hard materials and sharp edges of the components used in these systems may damage the separator film during the encapsulation process, or during removal of the encapsulated electrode from the encapsulation apparatus.

There are also no provisions for applying tension to the film to take up slack immediately prior to contact by the heating element of the apparatus, or for accommodating variances in thickness between electrodes being processed. Conventional systems are set up to encapsulate an electrode having the upper limit of the thickness tolerance. This results in some electrodes having encapsulating films that are loosely fitted.

What is needed, therefore, is a thermo-encapsulating apparatus and method that is capable of providing a tight fitting defect-free encapsulation of an electrode in a high melting point thermoplastic material.

SUMMARY OF THE INVENTION

The present invention meets the above-described needs by providing an apparatus and method for cutting and heat sealing polytetrafluoroethylene film and other high melting separator sheet materials enveloping individually shaped cathodes, anodes or other active components, for use in batteries or capacitors and other implantable medical devices.

The apparatus includes an electrode holding fixture and a heater assembly. The electrode holding fixture is comprised of a platen having an upper surface and a lower surface; an electrode holding die disposed on the upper surface of the platen and including an elastic body having an upper surface and a pocket formed in the elastic body. The pocket has an upper portion, a lower portion, and a wall surface shaped to correspond to the perimeter of the electrode. An electrode support is disposed in the lower portion of the pocket of the elastic body and comprises an upper surface and a lower surface.

The heater assembly is comprised of a dielectric base having an upper plate portion and a lower plate portion, the lower plate portion providing a heater channel formed therein; and a heating element including an upper portion disposed in the heater channel of the dielectric base and a lower portion extending beyond the lower surface of the base and comprising a cutting edge and a shoulder. A portion of the heating element is shaped to match a corresponding portion of the wall surface of the pocket of the elastic body. The heater assembly is operatively associated with the electrode holding fixture such that when they are pressed together, the cutting edge and shoulder of the heater element cuts and seals the separator material between the upper surface of the elastic body and the heater element. The dielectric base is preferably formed from a machinable ceramic material.

The electrode holding die may be further comprised of a base plate that is joined to the platen. The electrode support is preferably made of a dielectric material, and may be shaped to correspond to the perimeter of the electrode. The electrode support is also preferably movable within the pocket of the elastic body. When the electrode is wrapped or enveloped in the sheet of separator material and disposed in the pocket of the elastic body, the electrode support is forced against the sheet of separator material by at least one spring in contact with the lower surface of the electrode support.

In another embodiment, the apparatus includes an ejection tool for ejecting an electrode disposed in the pocket of the elastic body. The ejection tool comprises a piston disposed in a cavity in the electrode support, a shaft having an upper portion connected to the piston and passing through a hole in the electrode support, and a lower portion passing through a hole in the platen. The ejection tool is preferably connected to an actuator, which may include a lever and fulcrum assembly.

The elastic body of the electrode holding die may be made of a polysiloxane elastomer. The elastic body may further include a clearance notch extending from the wall surface of the pocket to the outer sidewall of the elastic body. The clearance notch is positioned to receive a wire contact extending from the electrode. The notch, in combination with an associated tab on the heating element, enables sealing of the separator sheet around the wire.

The apparatus preferably further comprises a film tensioning block mounted on the lower surface of the insulative base. The film tensioning block is operatively associated with the elastic body. When the heater assembly and electrode holding fixture are pressed together, the elastic body and the film tensioning block pinch the portion of separator material engaged between them and apply tension to the sheet of separator material wrapped around the electrode. In order for the tension to be more strongly applied to the separator material, a friction-reducing film such as polyamide may be disposed on the upper surface of the elastic body. The apparatus may also include a tool for immobilizing the proximal and distal ends of the sheet of separator material prior to pressing of the heater assembly and the electrode holding fixture together.

The heater assembly may be joined to a suspension plate, with standoffs disposed between them. In like manner, the electrode holding fixture may be joined to a mounting base, with standoffs separating them in order to limit heat conduction to the mounting base. The electrode holding fixture may also be mounted on a slide assembly so that it can be withdrawn from beneath the heater assembly to enable easy loading of an electrode and separator film into the pocket of the elastic body.

The present method for cutting and heat sealing a separator film around individually shaped electrodes is performed with the above apparatus and comprises placing a sheet of separator material on the upper surface of the elastic body; placing an electrode having a perimeter corresponding to the shape of the pocket upon the sheet of separator material in alignment with the pocket; forcing the electrode downwardly into the pocket, thereby drawing the separator sheet down into the pocket into contact with the electrode support; folding a distal portion of the separator sheet over the electrode and into contact with a proximal portion of the separator sheet; energizing the heating element; and bringing the heater assembly into contact with the electrode holding fixture with sufficient pressure to cut and seal the separator material between the upper surface of the elastic body and the heating element.

The apparatus and method of the present invention are advantageous over the prior art particularly because they are effective for processing high temperature separator materials requiring temperatures of from about 100° C. to about 500° C. for being thermally cut and sealed. That way, the present apparatus and method enables the manufacturing of electrodes enveloped in separator materials that have a relatively higher melting point, such as polytetrafluoroethylene, which is cut and sealed at a temperature of about 400° C. These separator materials are much more resistant to damage during subsequent high temperature manufacturing processes such as case welding. The present invention also results in the production of electrodes with more tightly fitting, defect-free separator films having a minimal flap or flashing at the electrode perimeter.

Additional objects, advantages, and characterizing features of the present invention will become increasingly more apparent upon a reading of the following detailed description together with the included drawings.

BRIEF DESCRIPTION OF THE DRAWINGS

The present invention will be described by reference to the following drawings, in which like numerals refer to like elements, and in which:

FIG. 5B is a detailed view of the clearance notch of FIG. 5A being deformed by the wire when a tab of the heating element presses downwardly on the wire;

FIG. 7B is a cross-sectional view of the cutting and sealing region of the heating element taken along line 7B-7B of FIG. 7;

The present invention will be described in connection with preferred embodiments, however, it will be understood that there is no intent to limit the invention to the embodiments described. On the contrary, the intent is to cover all alternatives, modifications, and equivalents as may be included within the scope of the invention as defined by the appended claims.

DETAILED DESCRIPTION OF THE PREFERRED EMBODIMENTS

In the following description, the terms "separator film," "separator sheet," and "sheet of separator material" are used interchangeably, and are meant to indicate a relatively thin material that provides physical separation between a first electrode and an associated opposite polarity electrode, thereby preventing a short circuit between the electrodes. Exemplary power sources comprising opposite polarity electrodes include a capacitor or a battery.

Figure 1:
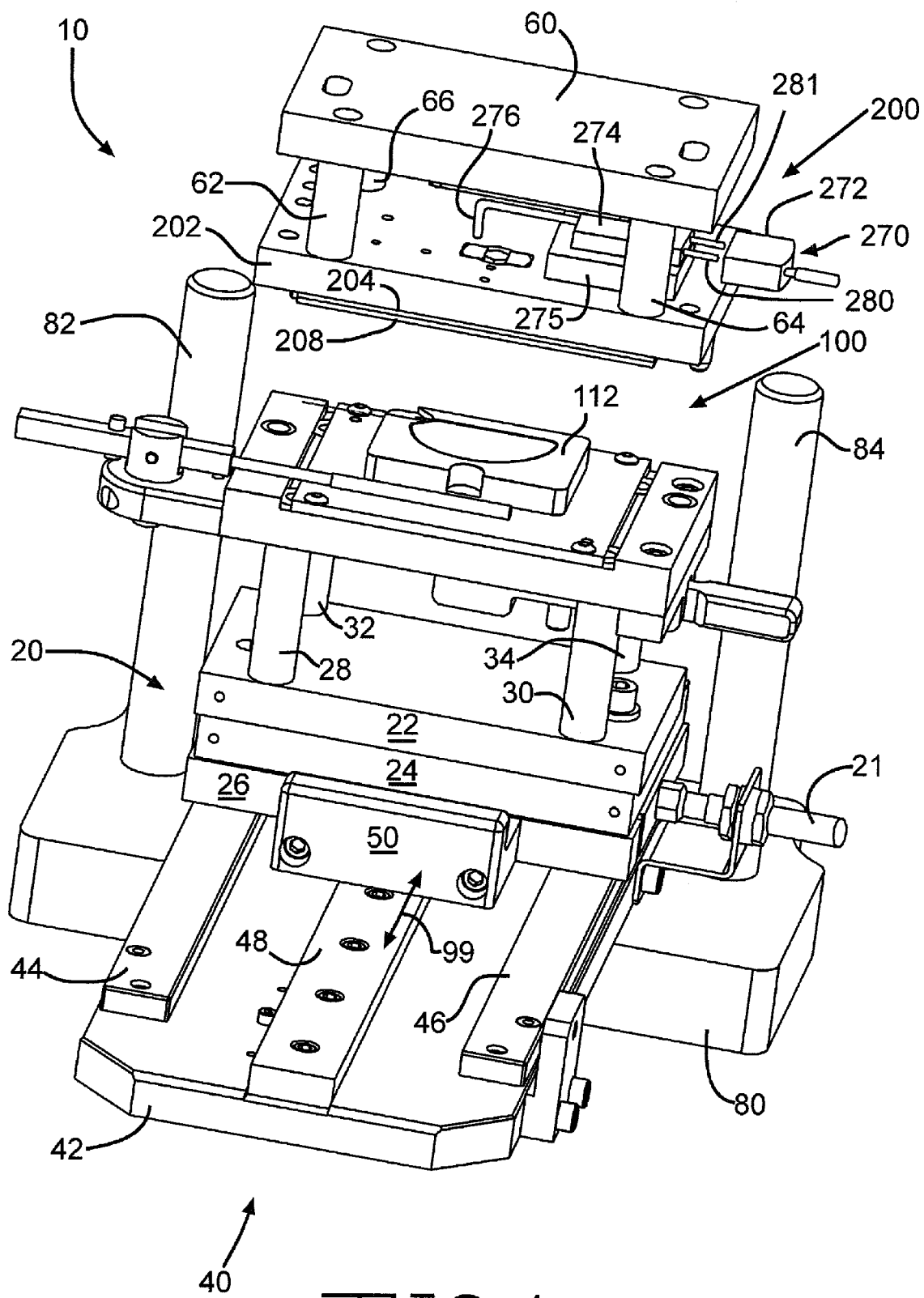
FIG. 1 is a perspective view of one apparatus for cutting and heat sealing a separator film around an electrode.
Figure 2:
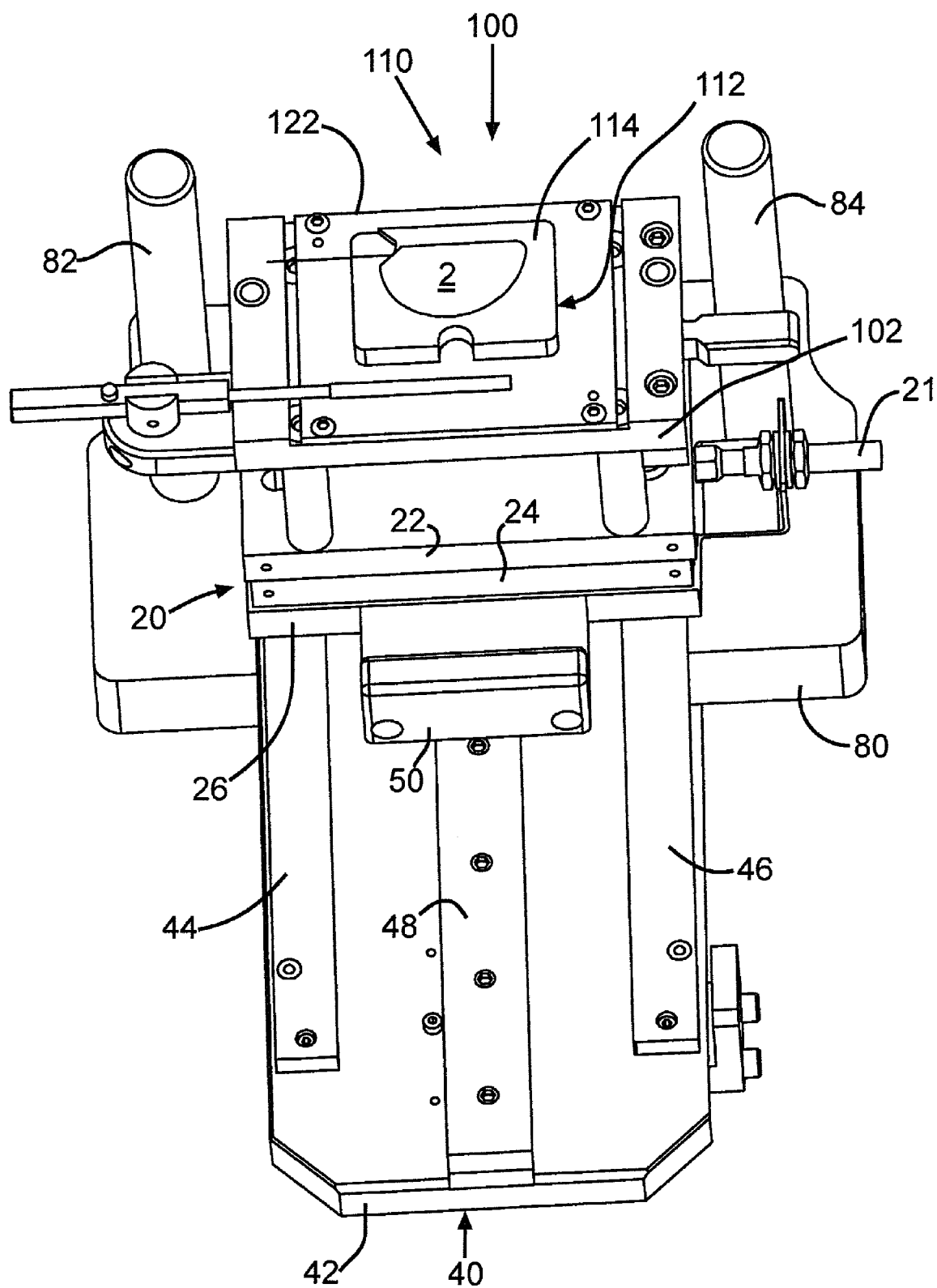
FIG. 2 is an upper perspective view of the electrode holding fixture of the assembly of FIG. 1, joined to a mounting base and mounted on a slide.
Figure 3:
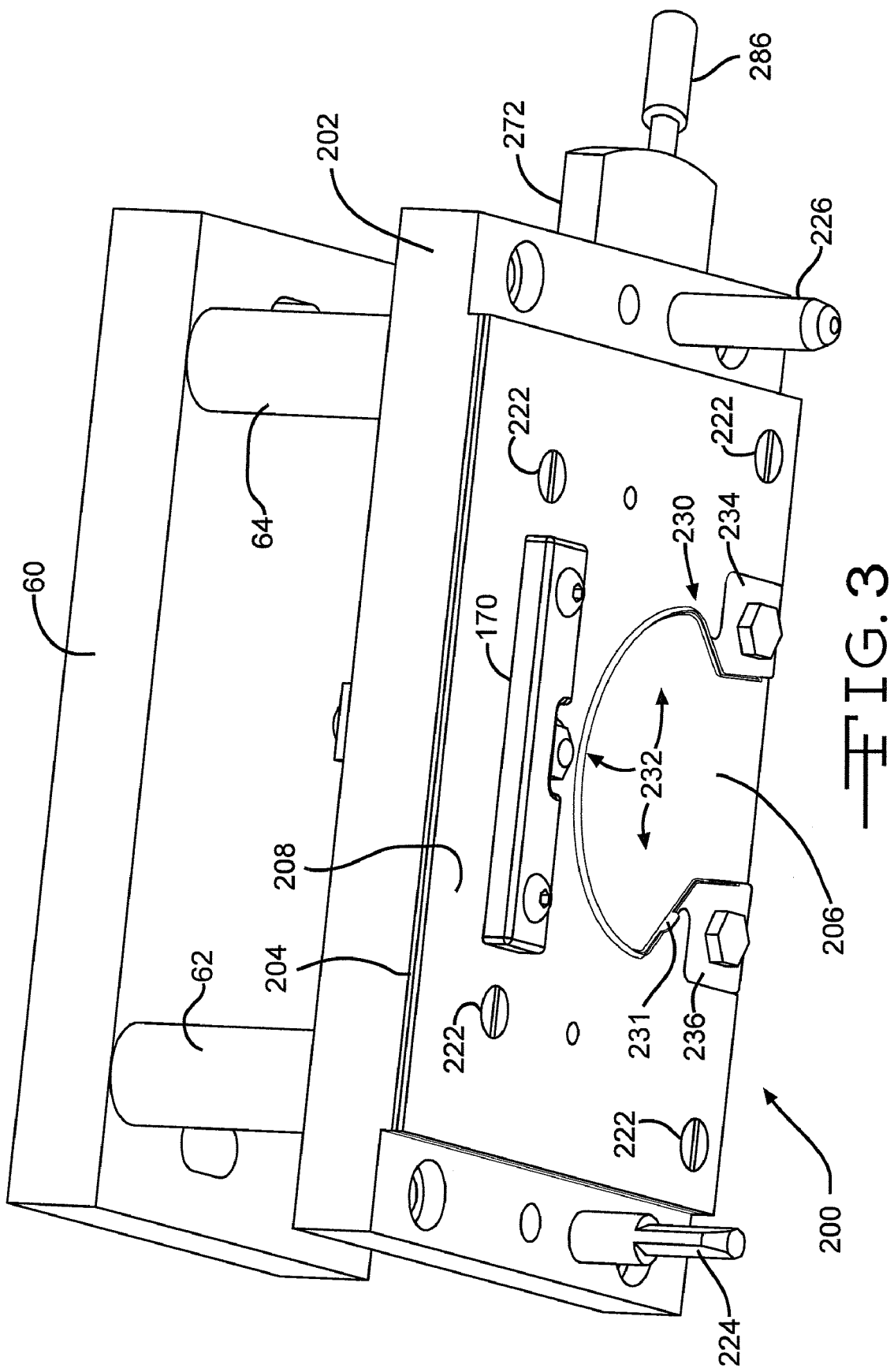
FIG. 3 is a lower perspective view of a heater assembly and suspension plate of the apparatus of FIG. 1.

Referring now to the drawings, FIGS. 1 to 3 illustrate the present thermo-encapsulation apparatus 10 comprised of an electrode holding fixture 100 and a heater assembly 200. The electrode holding fixture 100 may be joined to a mounting base 20 comprised of one or more rigid plates 22, 24 and 26. Electrode holding fixture 100 is preferably separated from mounting base 20 by standoffs 28, 30, 32 and 34 in order to thermally isolate the fixture 100 and to provide clearance for an electrode ejection tool 190, which will be subsequently described herein.

Electrode holding fixture 100 and mounting base 20 may also be mounted on a slide assembly 40 comprised of a plate 42, outer guide rails 44 and 46, and a center rail 48. Electrode holding fixture 100 is horizontally movable along plate 42, as indicated by bidirectional arrow 99. This is done by manipulating handle 50. In that manner, the electrode assembly 100 is withdrawn from beneath the heater assembly 200 to enable easy loading of an electrode and separator film therein. A proximity sensor 21 is provided to detect the correct positioning of the electrode holding fixture 100 beneath the heater assembly 200 prior to heat sealing.

The heater assembly 200 is preferably joined to a suspension plate 60 with standoffs 62, 64, 66 and 68 disposed there between. The standoffs thermally isolate heater assembly 200 from suspension plate 60.

The thermo-encapsulating apparatus 10 also comprises a main block 80 upon which the slide assembly 40 is mounted. The main block 80 further includes posts 82 and 84. A linear actuator (not shown) such as a pneumatic or hydraulic cylinder, or a linear stepper motor may be mounted on posts 82 and 84 and operatively connected to the heater assembly 200. The linear actuator is used to lower the heater assembly 200 and bring it into contact with the electrode holding fixture 100 during the heat sealing process.

The electrode holding fixture 100 will now be described with particular reference to FIGS. 2, 4 and 5. Electrode holding fixture 100 is comprised of a platen 102, an electrode holding die 110 and an electrode support 140. Platen 102 has an upper surface 104 and a lower surface 106. Electrode holding die 110 is disposed on the upper surface 104 of the platen 102 and includes a deformable body 112, preferably of an elastomeric material, having an upper surface 114 with a pocket 116 formed therein. The pocket 116 has an upper portion 118, a lower portion 119 and a wall surface 120 shaped to correspond to the perimeter 4 of an electrode 2.

Electrode holding fixture 100 is further comprised of the electrode support 140 disposed in the lower portion 119 of the pocket 116 of the elastic body 112. The electrode support 140 includes an upper surface 142 and a lower surface 144 and is preferably made of a dielectric material that is both electrically and thermally insulative. The electrode support 140 is preferably shaped to correspond to the perimeter 4 of the electrode 2 which it supports. That is to provide uniform support and thermal contact with electrode 2 during heat sealing. The dielectric material may be a machinable glass ceramic such as mica or MACOR®, which is manufactured and sold by Corning Inc. of Corning N.Y. Other structurally strong, heat-resistant ceramics that can be cast and fired to near net shape may also be used.

The electrode holding die 110 may be comprised of a base plate 122 that is joined to the platen 102 with suitable fasteners (not shown). The elastic body 112 is molded to the base plate 122. A recess or step 304 provided in the upper surface 104 of the platen 102 has a depth sufficient to receive the electrode holding die 110 therein. That sub-assembly has the spaced apart outer upper surfaces 306 of the platen 102 being substantially coplanar with the upper surface 124 of the holding die base plate 122.

The elastic body 112 is made of a heat-resistant elastomer having a relatively low thermal conductivity that is capable of recovering relatively quickly to its former shape from a deformation force. One preferred elastomer is a polysiloxane elastomer, commonly known as silicone rubber, having a Shore A durometer of between about 40 to about 90. Urethane is another suitable elastomer for this purpose.

Figure 6:
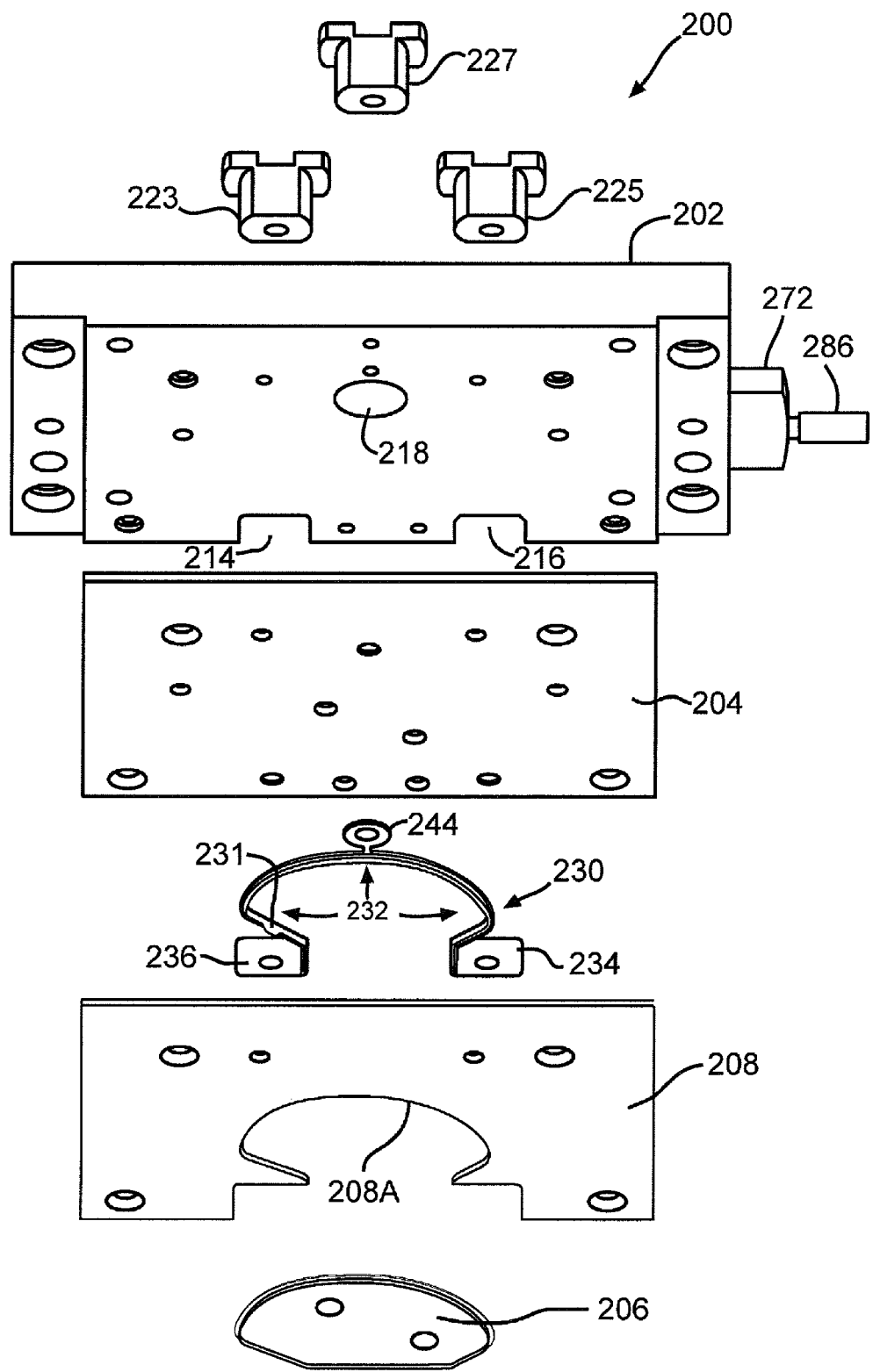
FIG. 6 is an exploded view of the heater assembly of FIG. 3.

Turning now to FIGS. 3 and 6, the heater assembly 200 is comprised of an upper platform 202 to which a base plate 204 of a dielectric material is secured by fasteners (not shown). Inner and outer hold-down plates 206 and 208 are, in turn, secured to the base plate 204 to hold a heating element 230 in place. The dielectric base plate 204 and the inner and outer hold-down plates 206, 208 are preferably formed from a machinable ceramic material, such as MACOR® or mica. Details of the heating element 230 are shown in FIGS. 6, 7, 7A and 7B. It is noted that in these drawings, the heating element 230 has been inverted from its installed position on the base plate 204 of the heater assembly 200. This was done to more clearly show key features thereby. As shown, the T-shaped heating element 230 is comprised of a cutting and sealing portion 232 that extends from terminal 234 to terminal 236. The cutting and sealing portion 232 includes a proximal head 238, a cutting edge 240 and a sealing shoulder 242. The cutting edge 240 and sealing shoulder 242 provide for cutting and sealing the separator film around the electrode, as will be explained subsequently. The head portion 238 includes relatively small flanges 238A, 238B that provide the heating element its T-shaped structure. The head portion 238 supported on the base plate 204 is held in position thereon by the edges 206A, 208A of the outer and inner hold-down plates 206, 208 capturing the respective flanges 238A, 238B.

Heating element 230 is formed approximately in an omega ($\Omega$) shape. Its cutting and sealing portion 232 is shaped to match a corresponding portion of the wall surface 120 of the pocket 116 of the elastic body (FIG. 5) which, in turn, corresponds to the shape of the electrode perimeter 4 being sealed in a separator film. In this manner, heating element 230 cuts and seals the separator film around the perimeter of the electrode except for the portion that is wrapped around the straight edge of the electrode, i.e., the "open" portion of the omega shape between the terminals 233 and 235.

Heating element 230 may also include an additional central terminal 244 for a more secure attachment to the base plate 204. Fasteners, which are partially shown in FIG. 3, engage with through holes in the terminals 234, 236 and 244 to secure the heating element 230 to the dielectric base 204. The relatively large terminals 234, 236 and 244 also provide for easy connection to power supply wires (not shown). Additionally, the terminals 234, 236 and 244 prevent hot spots in the heating element at the terminals, thereby providing better control of the heat sealing process.

The base plate 204 and the inner and outer hold-down plates 206, 208 are joined to the upper platform 202 by fasteners 222 (only shown for plates 204 and 208 in FIG. 3) that are preferably countersunk therein. Then, when there is a need in manufacturing to process electrodes with a different shape, only heating element 230 and the hold-down plates 206, 208 need to be changed. The platform 202 and the base plate 204 are provided with a sufficient number of threaded openings to accommodate such changeovers. In a like manner and with regard to the electrode holding fixture, only the electrode holding die 110 and the electrode support 140 need to be changed. That way, the manufacturing changeover to process a different electrode batch is made faster, simpler, and lower in cost compared to prior heat sealing systems.

The upper platform 202 of the heater assembly 200 is further provided with notches 214 and 216 (FIG. 6) and a large through hole 218 for receiving polymeric plugs 223, 225 and 227, respectively. The polymeric plugs 223, 225 and 227 provide stress relief to reduce the likelihood of cracking the dielectric base plate 204 at the fasteners.

Figure 8:
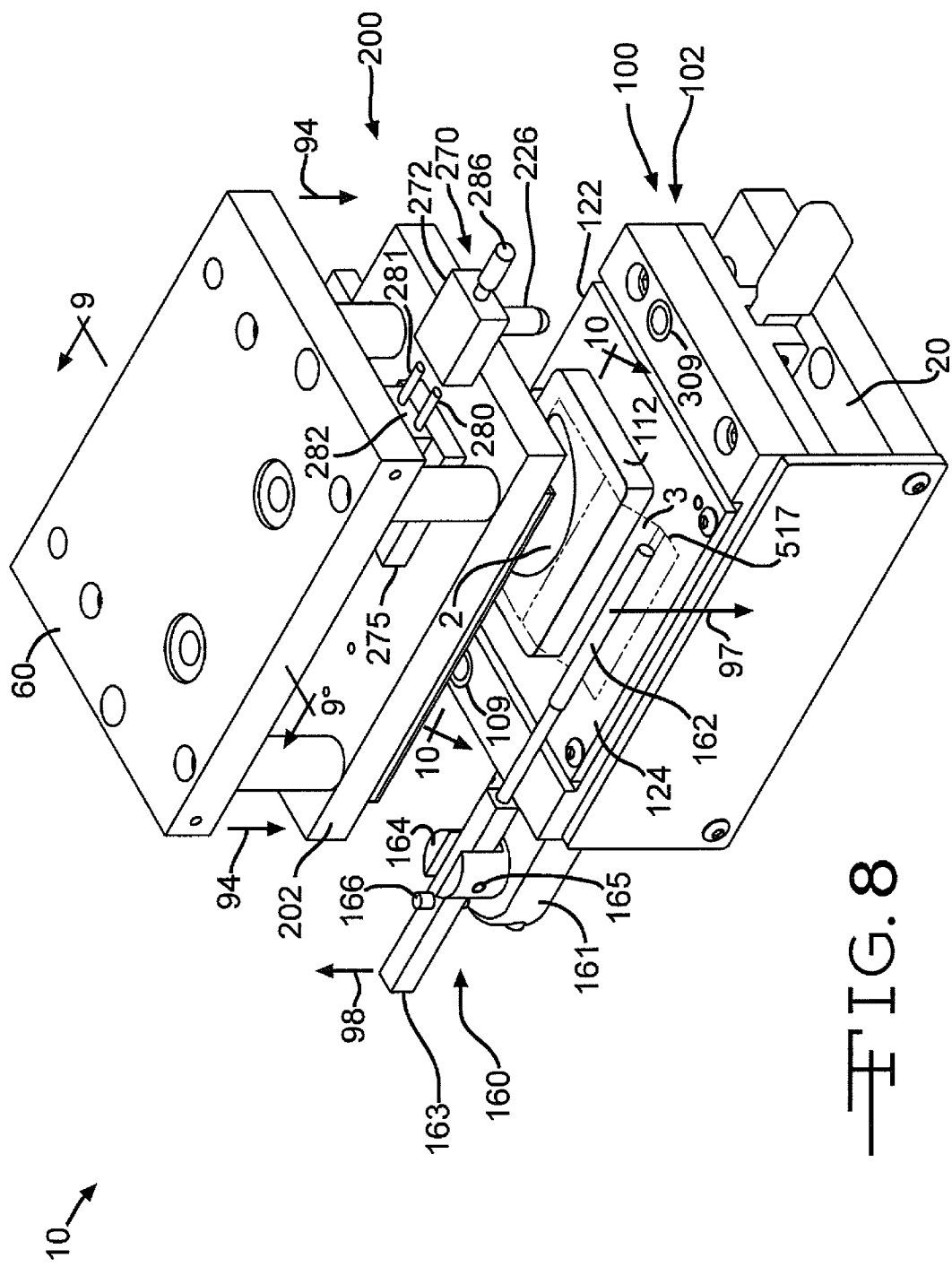
FIG. 8 is a perspective view of an apparatus for cutting and heat sealing a separator film around an electrode, shown with the electrode and separator film loaded in a pocket of the electrode holding die.

Certain additional preferred features of the thermo-encapsulating apparatus 10 will now be described along with the method for using the apparatus, and the advantages thereof. FIG. 8 is a perspective view of the apparatus shown with an electrode and separator sheet loaded in a pocket of the electrode holding die.

To begin the process, the electrode holding fixture 100 is withdrawn from beneath the heater assembly 200 using slide assembly 40 (FIG. 1). A piece of separator sheet 3 is placed over the pocket 116 in the elastic body 112 of the electrode holding die 110. An electrode 2 having a perimeter 4 corresponding to the shape of the pocket 116 is placed upon the sheet 3 in alignment with the pocket. The electrode 2 is then forced downwardly into the pocket 116. This draws the separator sheet 3 down into pocket. The separator sheet 3 is now in contact with the electrode support 140 and is contiguous with the wall surface 120 of the pocket 116 in the elastic body 112.

Figure 9:
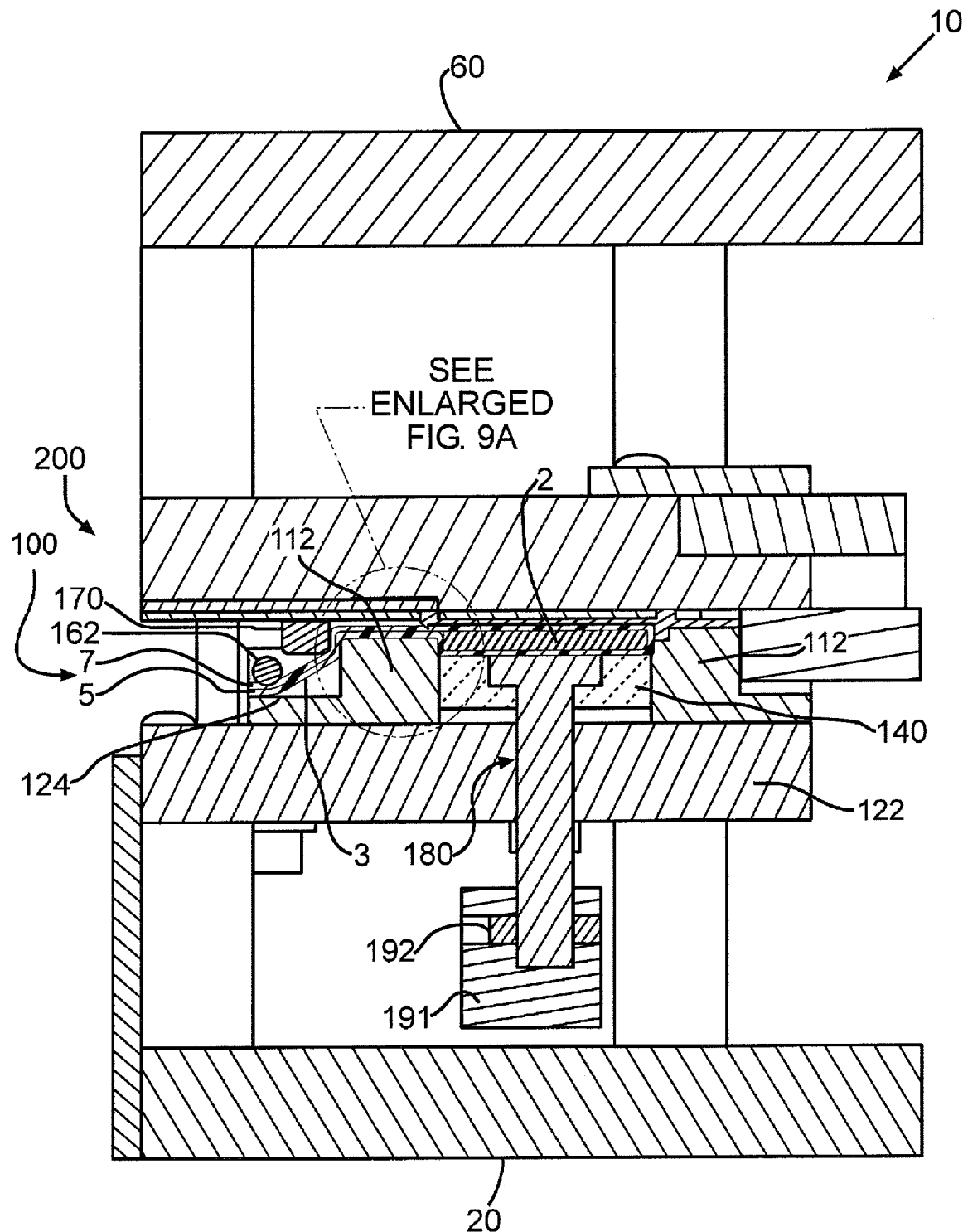
FIG. 9 is a cross-sectional view taken along the line 9-9 of FIG. 8.
Figure 9A:
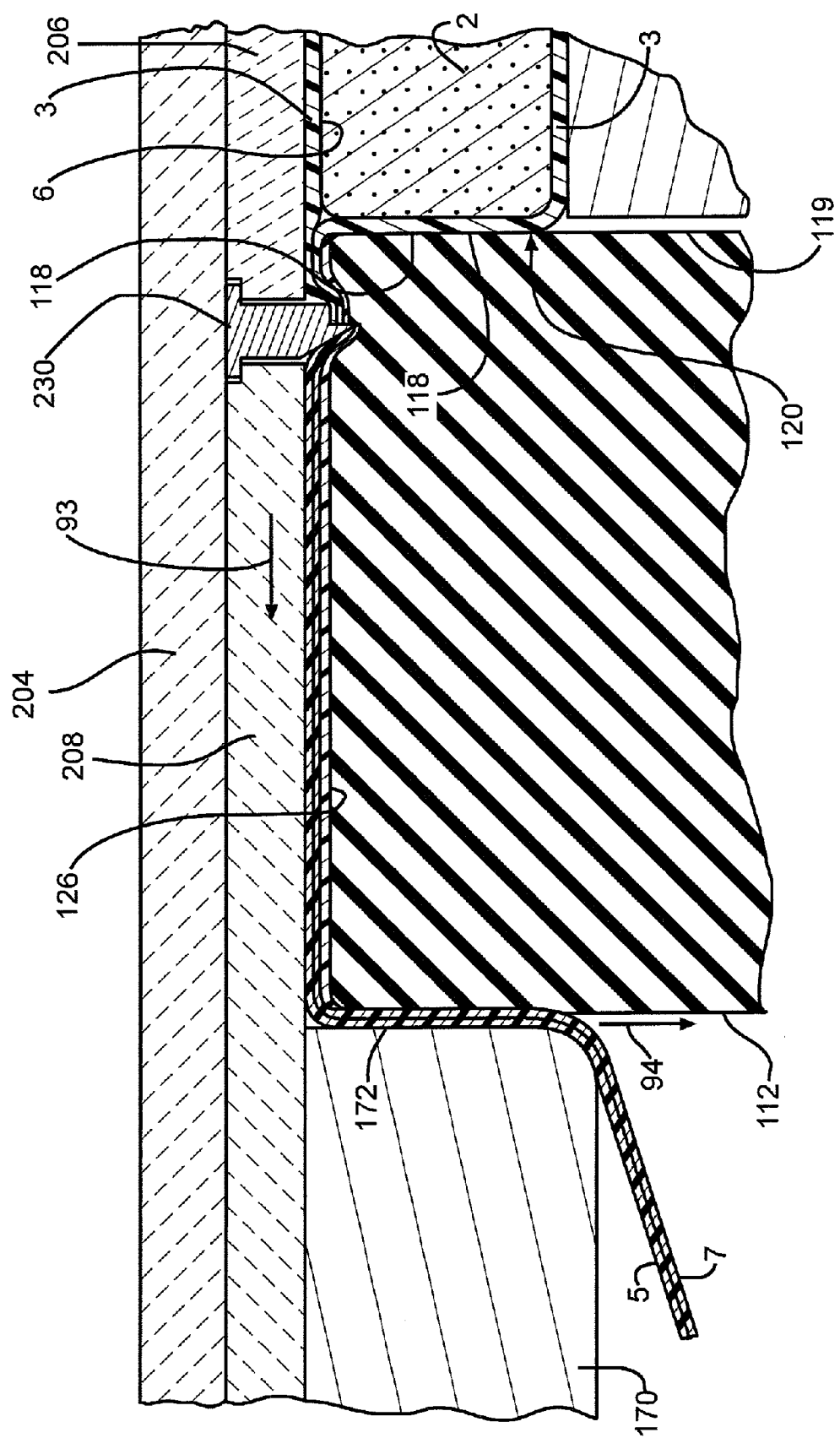
FIG. 9A is a detailed cross-sectional view of a first portion of the sealing region and a film tensioning block of the apparatus.

Referring also to FIG. 9A, a distal portion 5 of the separator sheet 3 is folded over the top surface 6 of the electrode 2, thereby fully enveloping electrode 2 in the separator sheet. Apparatus 10 preferably also includes a tool 160 (FIG. 8) for immobilizing the ends of the respective distal and proximal portions 5, 7 of the sheet 3 prior to pressing the heater assembly 200 and the electrode holding fixture 100 together. Holding tool 160 is comprised of an elongated rod 162 that is operatively connected to a handle 163. Handle 163 is joined to the fulcrum 164 by a pin 165. The fulcrum 164 is joined to the base 161, which in turn is joined to the platen 102. Tool 160 further comprises a spring loaded plunger 166 embedded in the handle 163.

To immobilize and hold the ends of the distal and proximal separator sheet portions 5, 7, handle 163 is pressed downwardly, thereby raising the elongated rod 162 above the upper surface 124 of the base plate 122. The ends of the distal and proximal portions 5, 7 of the sheet 3 are placed beneath rod 162, and the handle 163 is released. The plunger 166 then forces handle 163 upwardly, as indicated by arrow 98. By the action of fulcrum 164, the rod 162 is forced downwardly, as indicated by arrow 97, thereby pinching and immobilizing the ends of sheet 3 against the base plate 122.

It is noted that electrodes for electrochemical capacitors and batteries used to power implantable medical devices typically have a perimeter with at least one relatively straight portion. Referring also to FIGS. 4 and 5, pocket 116 in the elastic body 112 is provided with a corresponding straight portion 117 of wall 120, which is distally positioned with respect to the rod 162 of the holding tool 160. Thus, the fold of the separator sheet to form the wrap around electrode 2 is preferably made along the straight portion 117 and around the corresponding straight edge of electrode 2. In that manner, puckers and wrinkles in the separator sheet prior to sealing are minimized.

In the preferred embodiment, the electrode support 140 is also movable within the pocket 116 of the elastic body 112 and is continually forced upwardly. That way, when the electrode 2 is wrapped in the separator sheet 3 and disposed in the pocket 116 of the elastic body 112, the electrode support 140 is forced against the separator material. In that manner, electrodes having a substantial variation in their thickness can be processed in the apparatus 10 and tightly sealed in the separator film.

Figure 4:
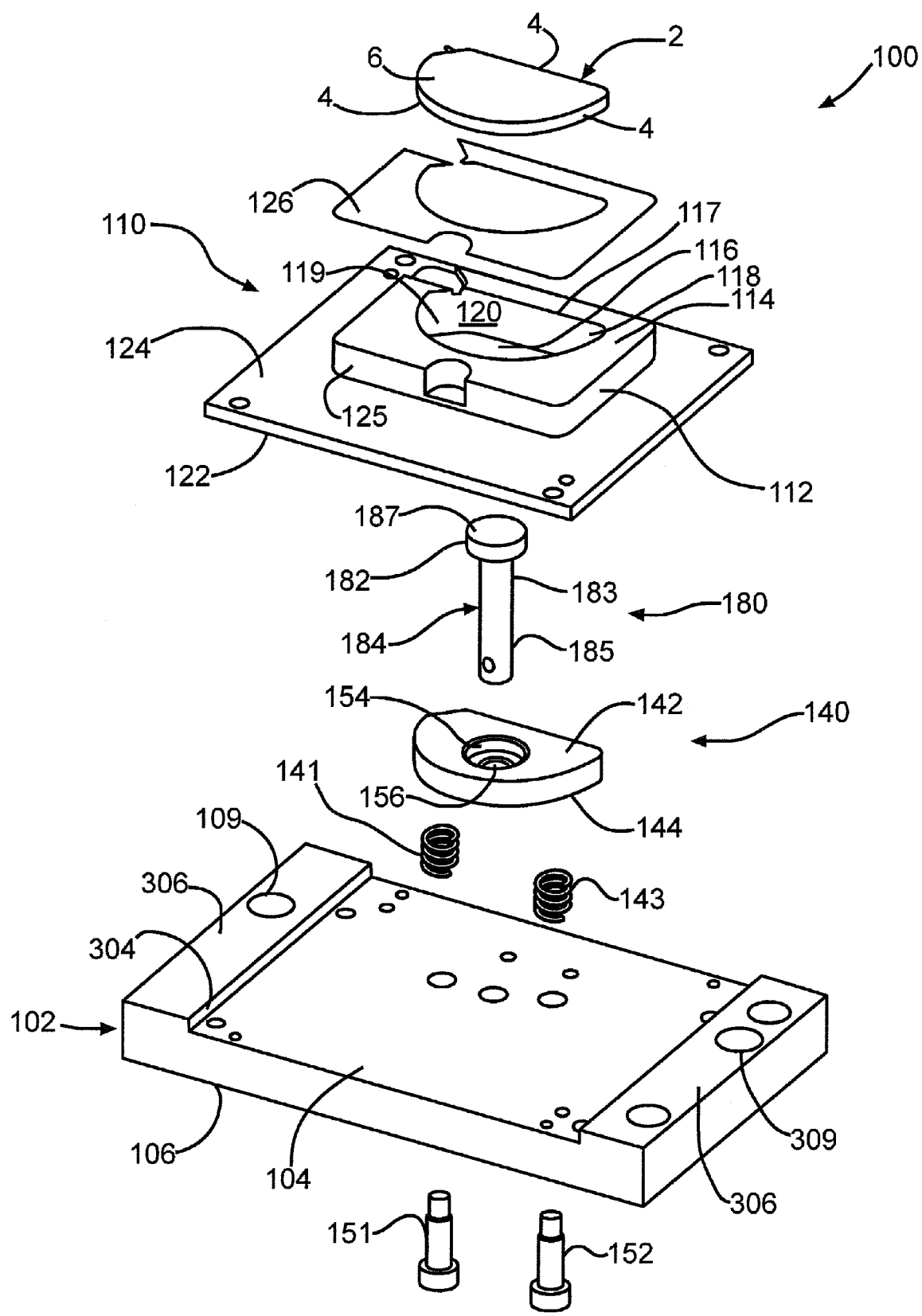
FIG. 4 is an exploded view of the electrode holding fixture of FIG. 2.
Figure 5:
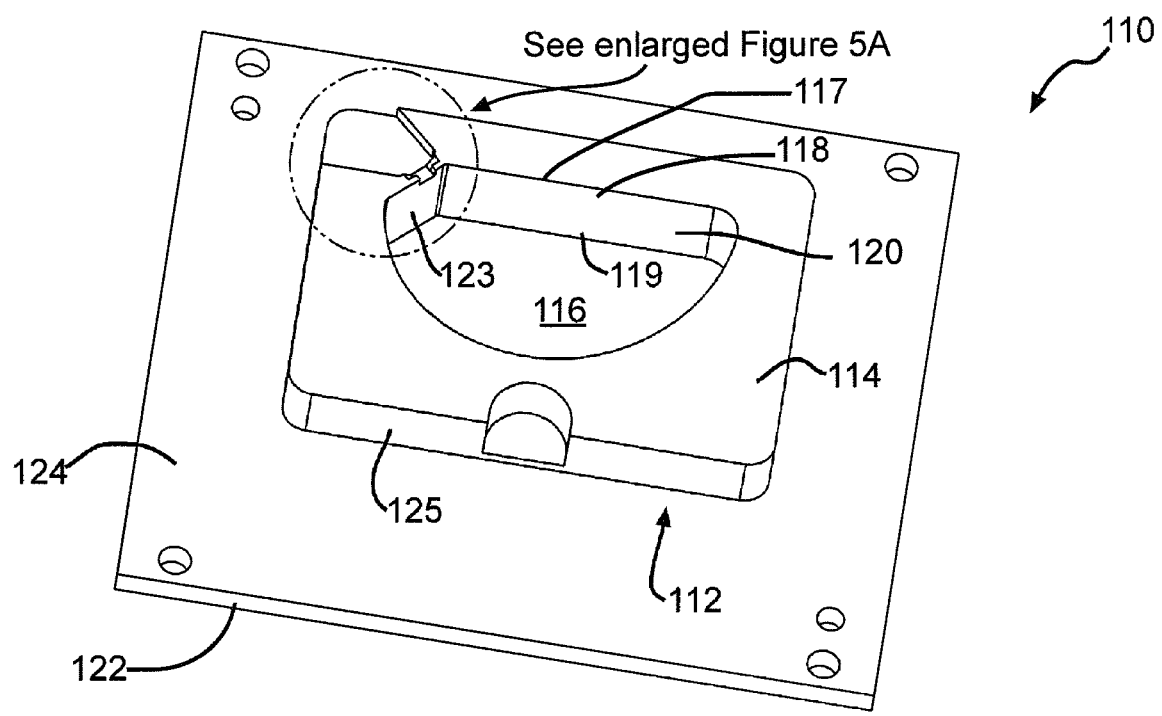
FIG. 5 is a perspective view of the electrode holding die of the electrode holding fixture of FIG. 2.
Figure 10:
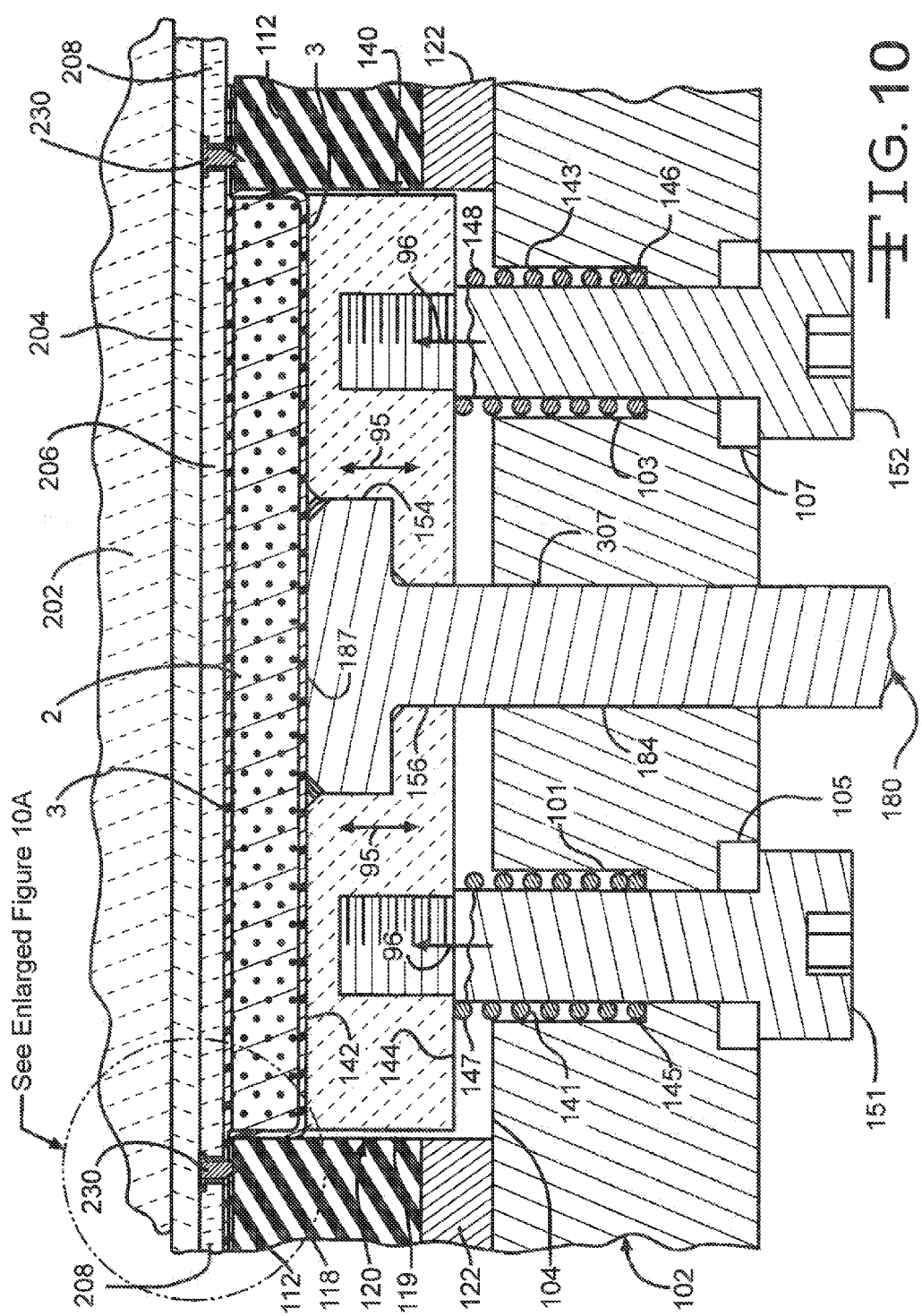
FIG. 10 is a cross-sectional view of the apparatus taken along line 10-10 of FIG. 8, and depicting the piston of the electrode ejection tool and the electrode support forced against the separator film and the lower surface of the electrode.

Referring in particular to FIGS. 4 and 10, springs 141 and 143 are provided for applying an upward force on the electrode support 140. The respective outer ends 145 and 146 of the springs 141 and 143 abut against the bottoms of respective upper counterbores 101 and 103 in the platen 102. The respective inner ends 147 and 148 of the springs 141 and 143 are in contact with the lower surface 144 of the electrode support 140 to thereby apply an upward bias thereto, as indicated by arrows 96. Shoulder bolts 151 and 152 pass through holes that continue in platen 102 from the upper counter bores 101 and 103 to the lower counterbores 105 and 107. The shoulder bolts 151 and 152 are engaged with threaded holes in the electrode support 140 and serve as locators for maintaining the springs 141 and 143 in position.

As indicated by bidirectional arrows 95, electrode support 140 thus "floats" within the lower portion 119 of the pocket 116. Its upward travel is stopped when the heads of bolts 151 and 152 bottom out in the lower counterbores 105 and 107, and its downward travel is stopped when surface 144 contacts surface 104 of the platen 102. When electrode 2 and separator sheet 3 are first loaded into pocket 116, the upper surface 6 of the electrode 2 is above the upper surface 114 of the elastic body 112, and the bolt heads 151 and 152 bottom out in the lower counterbores 105 and 107. However, during the heat sealing step, when the heater assembly 200 is pressed against the electrode holding fixture 100, the lower surface 206 of the housing plate 220 pushes down on the separator sheet 3 and electrode 2 until the upper electrode surface 6 is substantially coplanar with the upper surface 114 of the elastic body 112. This occurs regardless whether there is a substantial thickness variation between individual electrodes being sealed, with springs 141 and 143 compressing as needed to adjust the position of electrode support 140. (However, the maximum electrode thickness is ultimately limited to the depth of the pocket minus the sum of the electrode support and twice the separator sheet thickness.)

It is also noted that the fit of the electrode 2 and separator film 3 in pocket 116 is snug, thereby providing a very tight fit of the separator film around the electrode as compared to prior art sealing apparatus. However, the silicone rubber material of the elastic body 112 is sufficiently soft so that in spite of the tight fit, damage to the separator sheet 3 by the relatively hard electrode 2 is minimized.

It will be apparent that other spring arrangements can be used to achieve the same result of a floating electrode support. For example, the electrode support 140 and the platen 102 can be configured to have a single spring disposed in a counterbore around the shaft 184 of the ejection tool 180. Alternatively, other springs such as leaf springs could be used.

With the electrode 2 and separator sheet 3 loaded into the pocket 116 of the elastic body 112, and with the ends of the separator sheet held down, the heat sealing step is now performed. The electrode holding fixture 100 is replaced beneath the heater assembly 200 using slide assembly 40. The heating element 230 is energized by an electrical power supply (not shown) and heated to the desired temperature. Referring now to FIG. 8, heater assembly 200 is lowered, as indicated, by a suitable linear actuator (not shown), until the heating element 230 contacts the separator material on the upper surface 114 of the elastic body 112. Heater assembly 200 is preferably provided with a pair of guide pins 224 and 226 (FIG. 3). Guide pin has a "key" shape while guide pin 226 has a cylindrical shape and they engage with respectively shaped holes 109 and 309 in the platen 102. In this manner, the heating element 230 is precisely brought into contact with the upper surface 114 of the elastic body 112 in the required position with respect to the perimeter 4 of electrode 2.

Figure 8A:
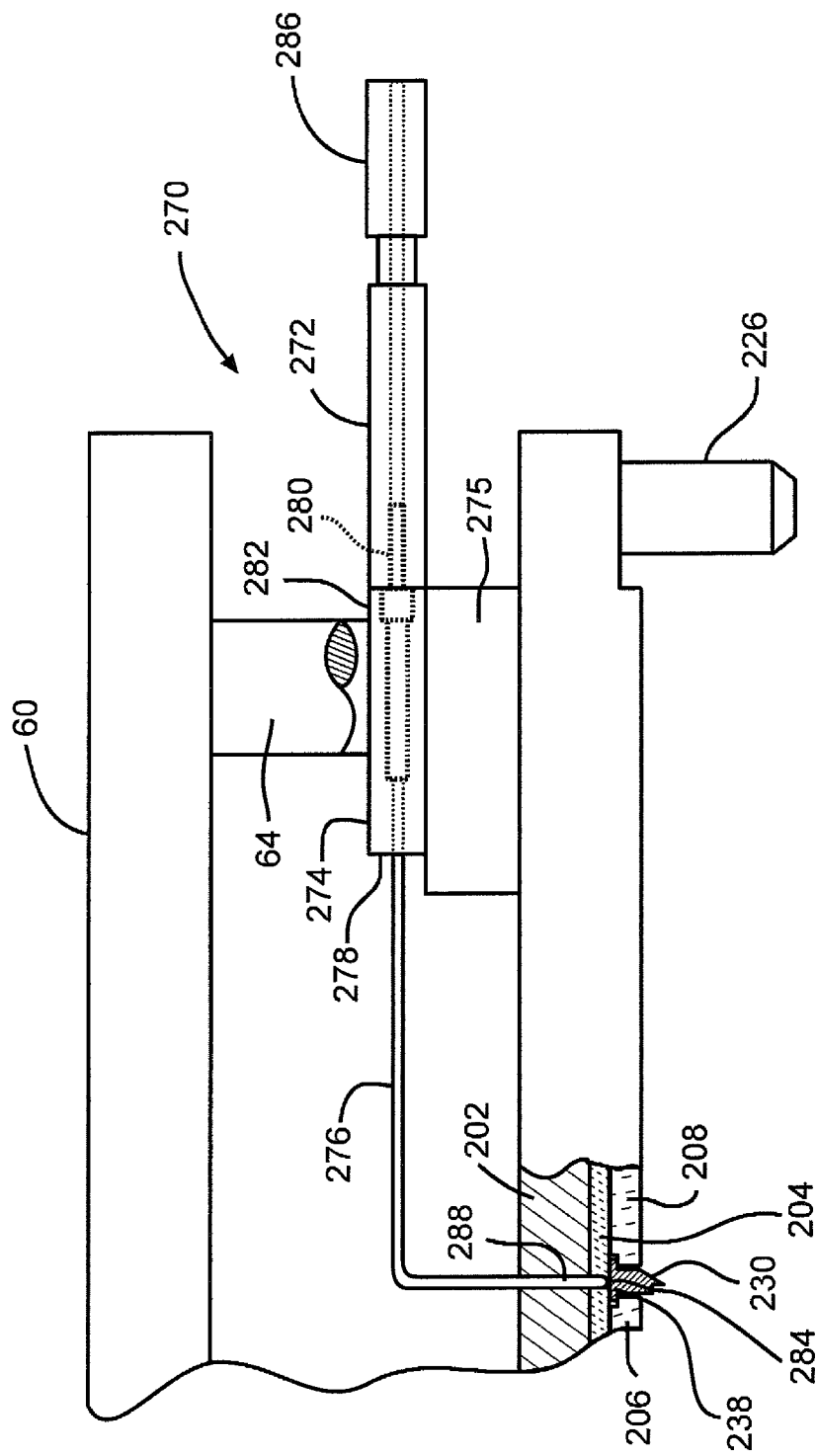
FIG. 8A is a side elevation view of a portion of the heater assembly and suspension plate of the apparatus of FIG. 1, with a partial cutaway view showing the contact between a thermocouple and the upper surface of the heating element.

Referring also to FIG. 8A, the thermo-encapsulating apparatus 10 may also include a temperature sensing device, such as thermocouple probe 270, that is provided for measuring and controlling the temperature of the heating element 230. This is important because the present thermo-encapsulating apparatus 10 is useful for enveloping an electrode structure in a variety of separator materials having a wide range of melting temperatures. Typical separators are of a polymeric material requiring temperatures of from about 100° C. to about 500° C. for being thermally sealed. One preferred material is polytetrafluoroethylene, which is sealed at a relatively high temperature range of about 200° C. to about 500° C., preferably about 400° C. Polyethylene is another preferred separator material that is sealed at a temperature range of about 130° C. to about 250° C. However, those skilled in the art will be able to readily determine at what temperature a particular polymeric material melts. That way, the present apparatus 10 makes it possible to regulate the temperature at which the separator sheet portions 5, 7 are fused to each other during the sealing step of the process.

Thermocouple probe 270 is comprised of a female connector 272, a male connector 274, and a protective sheath 276 extending from the distal end 278 of connector 274. The male connector 244 may be secured to a mounting block 275, which in turn is secured to upper dielectric plate 203 by suitable fasteners (not shown).

A pair of thermocouple wires (not shown) is connected to spades 280, 281 that extend from the proximal end 282 of the male connector 274. These thermocouple wires are insulated, and extend through the protective sheath 276, which is typically a thin-walled metallic tube. Within the distal tip 284 of sheath 276, the thermocouple wires are joined to form the thermocouple junction, which is the point at which the temperature measurement is made by probe 270. The thermocouple wires may be made of chromel and alumel alloys, thereby providing a K-type thermocouple.

Spades 280 and 281 are insertable into corresponding receptacles that are connected to a pair of terminals (not shown) in female connector 276. Additional thermocouple wires (not shown) are connected to these respective terminals, and extend out through a strain relief bushing 286. These thermocouple wires in turn are connected to a thermocouple circuit board (not shown) that detects the voltage potential produced at the thermocouple junction and converts the potential into temperature data. This type of thermocouple instrument is well known and is manufactured and sold commercially by various companies such as Omega Engineering of Stamford, Conn.

Small bores (not shown) are provided through the upper platform 202 and the base plate 204 for receiving the distal portion 288 of sheath 276. The distal portion 288 extends downwardly through the bores so that its distal tip 284 is in direct contact with the proximal head 238 of the heating element 230. In that manner, an accurate and responsive measurement of the temperature of the heating element 230 can be made by the thermocouple probe 270. In one preferred embodiment, the proximal head 238 of heating element 230 and at least the distal portion 288 of the sheath 276 are coated with a thin film of electrically insulative and thermally conductive material that is unaffected by high temperatures. One suitable thin film coating is diamond-like carbon (DLC).

It will be apparent to those skilled in the art that other known temperature measurement probes may be used instead of probe 270 to measure the temperature of heating element 230. For example, a platinum resistance thermometer (PRT) may be used in a similar configuration.

Figure 10A:
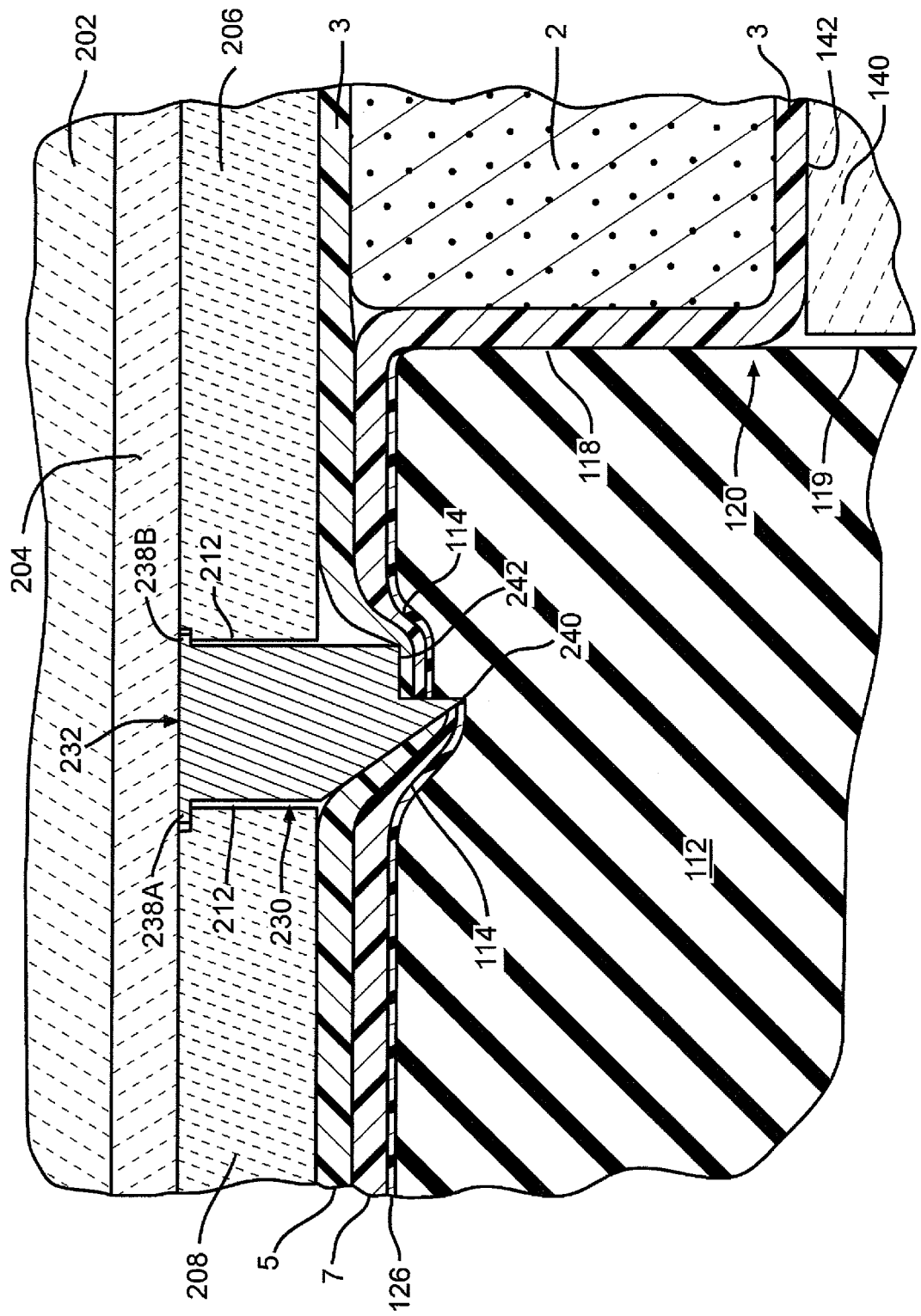
FIG. 10A is a detailed cross-sectional view of a second portion of the sealing region of the apparatus.

FIG. 10A is a detailed cross-sectional view of the pressing of the sealing portion of the heating element against the separator sheet and the elastic body 112 near the perimeter of the electrode. As the cutting edge 240 of the heating element 230 cuts the overlapping layers 5 and 7 of separator sheet, the sealing shoulder 242 faces the electrode 2 and firmly presses a narrow band of the separator layers together. Then, the layers 5 and 7 are fused together under high pressure and heat at the shoulder 242, thereby enveloping the electrode 2 within the separator sheet 3. It can be seen that the upper surface 114 of the elastic body 112 near heating element 230 is elastically deformed during cutting and sealing. This deformation is reversed when the heating element 230 is removed.

The apparatus preferably further comprises a film tensioning block 170 mounted on the outer hold-down plate 208. The tensioning block is operatively associated with the elastic body 112. When the heater assembly and the electrode holding fixture are pressed together, the elastic body 112 and the film tensioning block 170 pinch the separator portions 5, 7 together and apply tension to the separator material wrapped around the electrode 2.

Referring to FIGS. 3, 9 and 9A, film tensioning block 170 is joined to the outer hold-down plate 208. The inner sidewall 172 of the tensioning block 170 is positioned with respect to the outer sidewall 121 of the elastic body 112 so that when the heater assembly 200 and electrode holding fixture 100 are pressed together, a gap is formed between them. The gap width is slightly less than two times the thickness of the separator film, so that the distal and proximal separator sheet portions 5, 7 are pinched between the sidewalls 121 and 172 during downward motion of the tensioning block 170, as shown in FIG. 9A. This downward motion results in a downward pulling of the distal and the proximal portions 5, 7 of the separator sheet 3, as indicated by arrow 94. This, in turn, results in tensioning of the distal and proximal separator portions 5, 7 around the electrode 2, as indicated by arrow 93. It is to be understood that the tensioning of the separator portions 5, 7 occurs immediately prior to contact of the heating element 230 with them, while they are still free to be displaced horizontally. Then, the cutting and sealing portion 232 of heating element 230 "bites" into the separator portions 5, 7, cuts and seals them together as described previously. In this manner, a superior fit of the sealed separator sheet 3 to the electrode 2 is achieved.

As shown in FIG. 10A, in order for the tension to be more strongly applied to the separator material, a friction-reducing film 126 is provided on the upper surface 114 of the elastic body 112. The friction reducing film has a lower coefficient of friction than the relatively "tacky" silicone rubber material of the elastic body 112. This enables the proximal portion 7 of the separator material 3 to more easily slip along upper surface 114 during tensioning. In one embodiment, the friction reducing film is a polyimide.

Figure 5A:
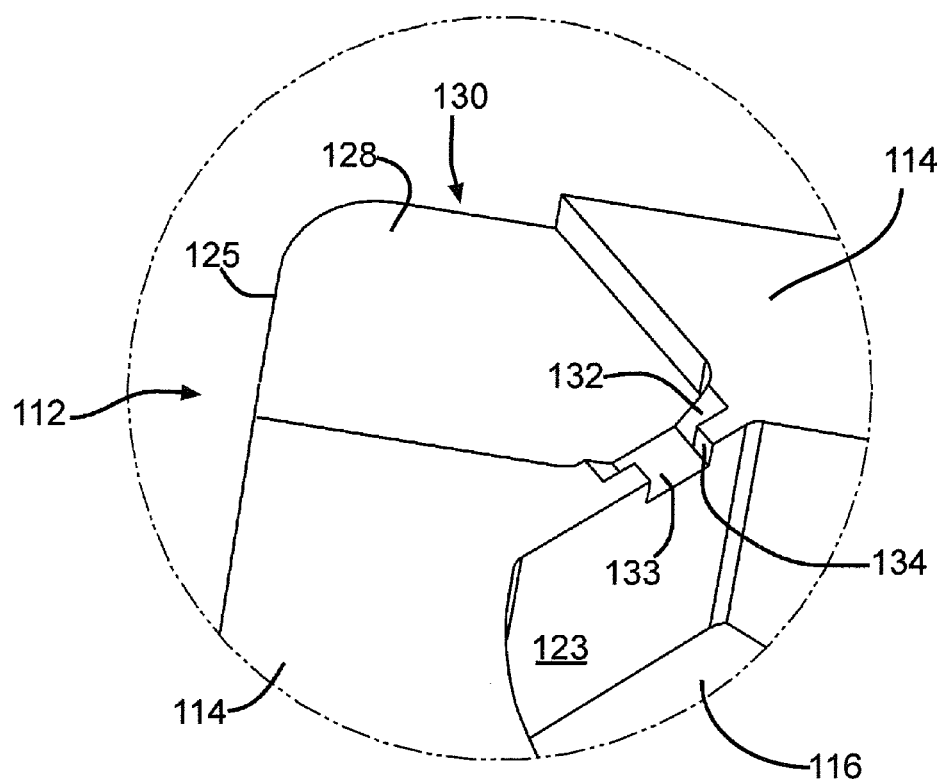
FIG. 5A is a detailed view of a clearance notch in the electrode holding die positioned to receive a wire extending from an electrode.

In a preferred embodiment, the elastic body of the electrode holding die includes a clearance notch positioned to receive a wire contact extending from the electrode. The notch, in combination with an associated tab on the heating element, enables sealing of the separator sheet around the wire. Referring to FIGS. 5, 5A and 5B, clearance notch 130 is located in elastic body 112 in a position corresponding with the contact wire 9 extending laterally from the electrode 2. This is typically in the "corner" of the electrode, i.e. where the straight edge of the electrode intersects the curved portion. Clearance notch 130 extends from pocket wall surface 123 to the outer sidewall 125 of the elastic body 112 and includes a recessed portion 128, a wire sealing portion 132 and a barrier portion 134.

The bottom surfaces of wire sealing portion 132 and barrier portion 134 form a contiguous surface 133. The wire 9 rests upon the separator sheet when the electrode 2 and the separator sheet 3 are first placed in the pocket 116 of the elastic body 112. The separator sheet, in turn, rests upon notch surface 133. (For the sake of simplicity of illustration, and in order to depict the interaction of wire 9 with notch 130, the separator sheet is not shown in FIG. 5B.)

Figure 7:
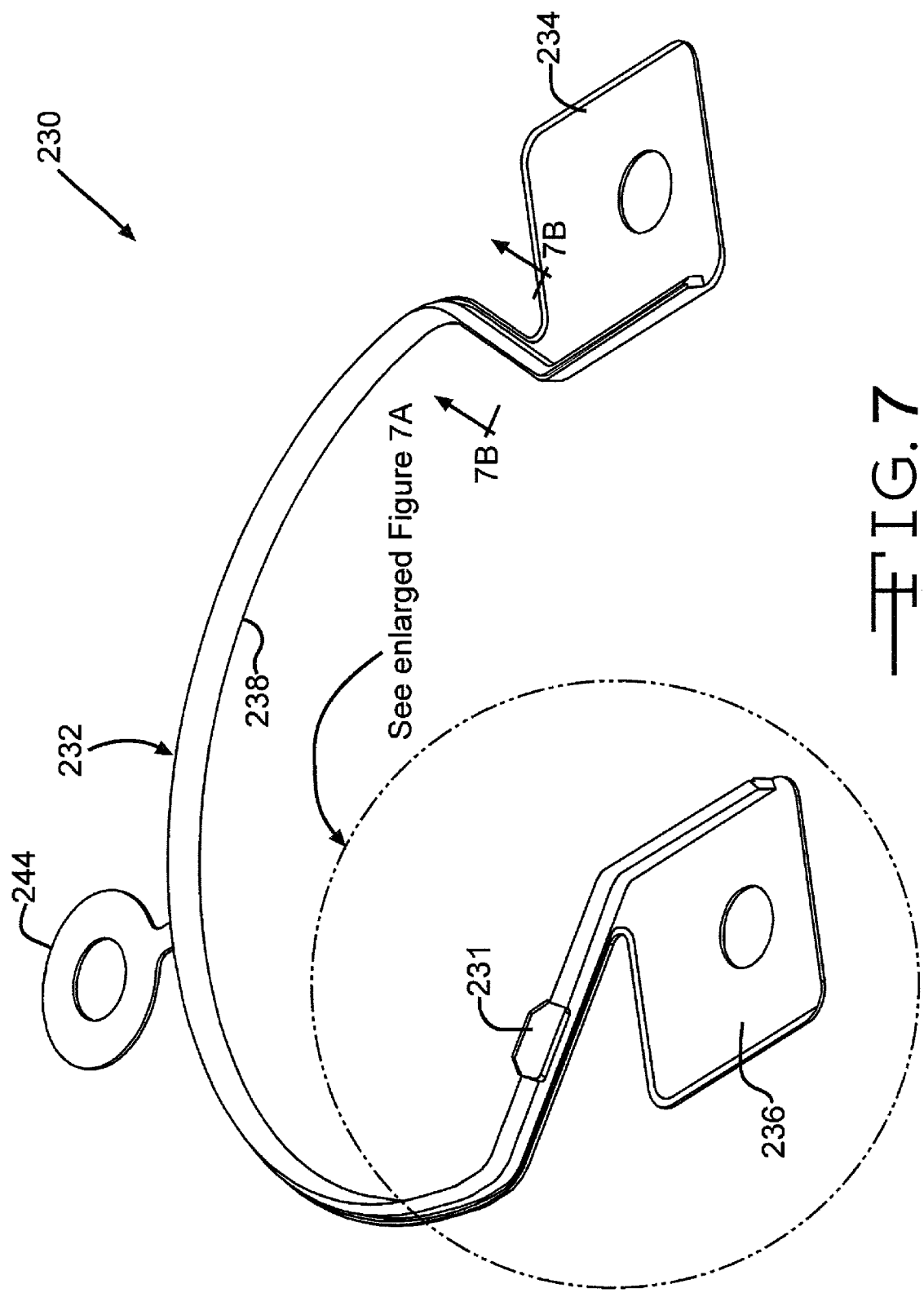
FIG. 7 is a perspective view of a heating element used in the heater assembly.
Figure 7A:
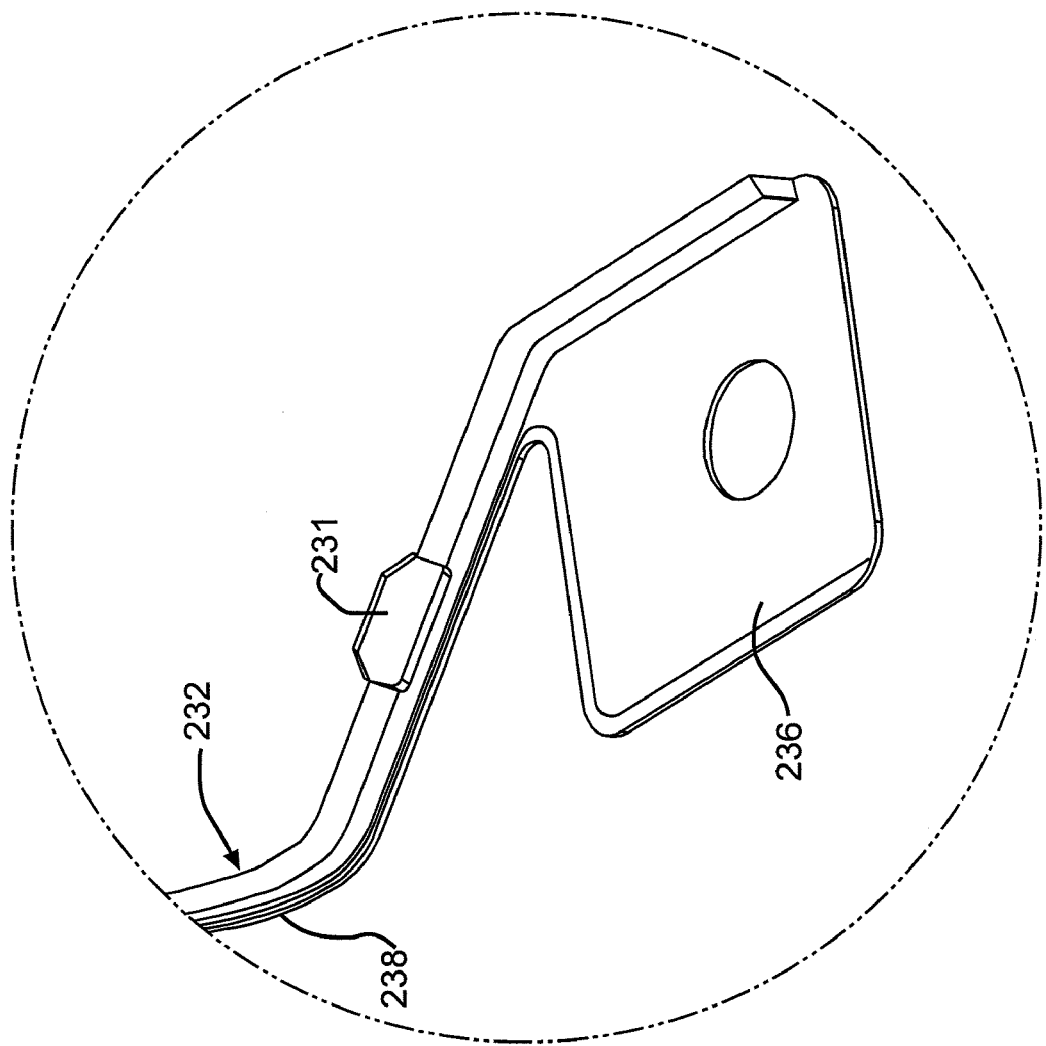
FIG. 7A is a detailed view of a terminal of the heating element of FIG. 7.

Referring also to FIGS. 3 and 7, heating element 230 is provided with a wire sealing tab 231 that is shaped to match the surfaces of the wire sealing portion 132 of clearance notch 130. When heater assembly 200 is lowered and heating element 230 contacts the separator portions 5, 7 and the upper surface 114 of the elastic body 112, sealing tab 231 contacts electrode wire 9 and pushes downwardly on it. The surface 133 of notch 130 deforms elastically as shown in FIG. 5B, and the separator portions 5, 7 (not shown) disposed above and below wire 9 correspondingly deform as well. The heat from sealing tab 231 fuses the portions 5, 7 together proximate to the wire 9. This provides a superior seal of the separator material around the wire 9. The barrier portion 134 of notch 130 is made sufficiently narrow to prevent unwanted heat transfer inwardly from sealing tab 231 to the electrode 2.

The electrode 2 may include a J-bend 11, a glass-to-metal-seal 12 and contact wire 14 joined to electrode wire 9 prior to the separator heat sealing process. These contacts are disposed in recessed portion 128 of the clearance notch 130 during sealing. If the glass-to-metal seal 12 is larger than the depth of the recessed portion 128, the elastic body 112 will temporarily deform as needed where the seal contacts the recessed portion 128.

With the separator sheet 3 having been cut and sealed around the electrode 2 as described, the heater assembly 200 is now withdrawn upwardly from the electrode holding fixture 100. The electrode holding fixture 100 with the electrode 2 sealed in the separator sheet 3 is withdrawn from beneath the heater assembly 200 using slide assembly 40 (FIG. 1). The sealed electrode 2 is then removed from the pocket 116 of the elastic body 112.

Figure 11:
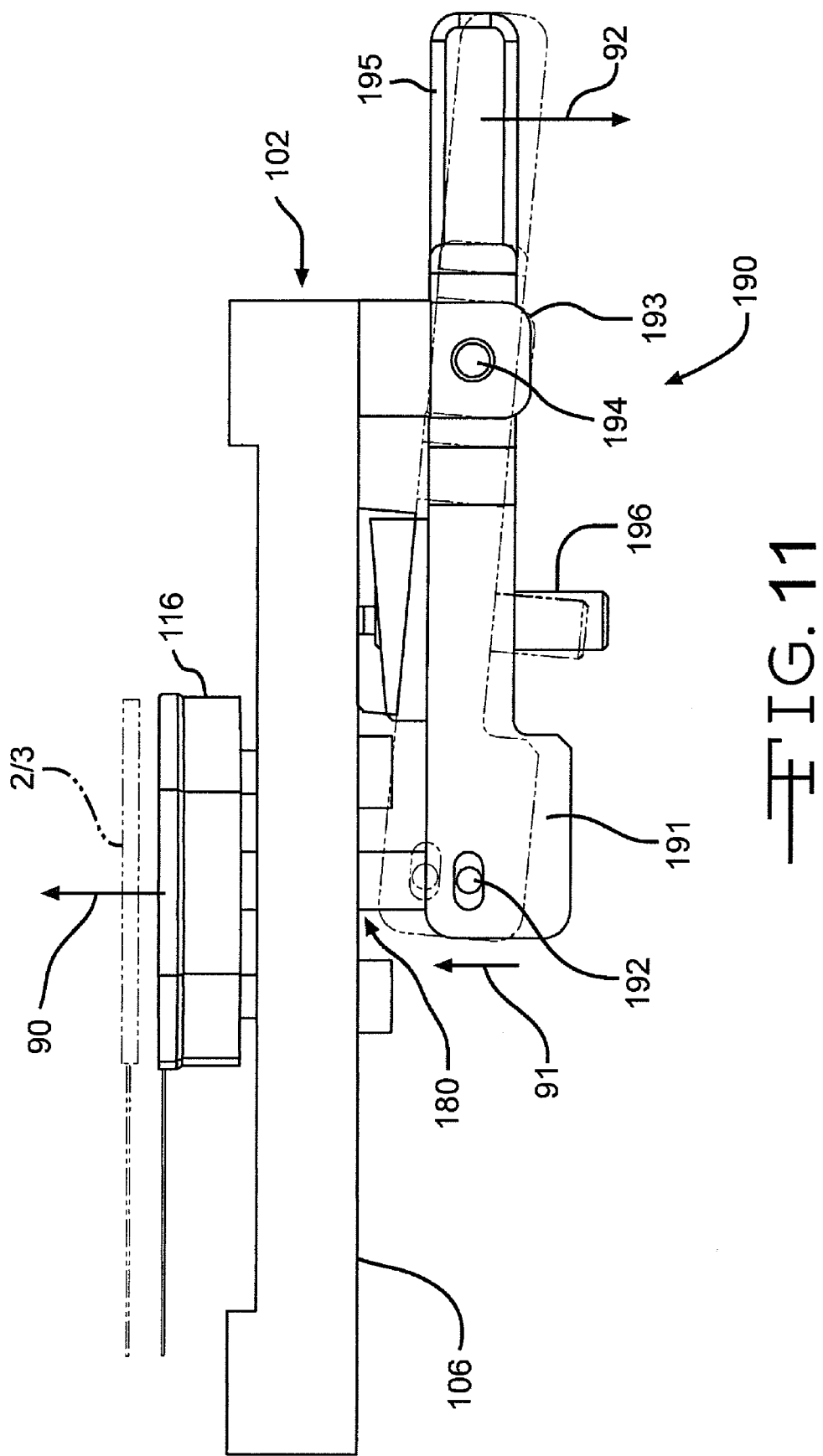
FIG. 11 is a side elevation view of the ejection tool and actuator for ejecting an electrode disposed in the pocket of the elastic body.

Because of the tight fit of the electrode 2 and enveloping separator sheet 3 in the pocket 116 of the elastic body 112, the thermo-encapsulating apparatus 10 preferably includes an ejection tool 180 for ejecting the sealed electrode from the pocket. Referring to FIGS. 4, 9 and 11, the ejection tool 180 is comprised of a piston 182 disposed in a cavity 154 in the electrode support, a shaft 184 having an upper portion 183 connected to the piston 182 and passing through a hole 156 in the electrode support, and a lower portion 185 passing through a hole 307 in the platen 102 of the electrode holding fixture 102. The upper surface 187 of piston 182 is made large with respect to the size of electrode support 140, and is provided with a radiused edge. These features prevent damage to the separator sheet 3 during ejection of the sealed electrode 2.

Although the ejection tool 180 may be operated by contact with an operator's finger, it is preferably connected to an actuator for easier operation. Referring to FIGS. 9 and 11, actuator 190 is comprised of a lever 191 that is connected to the ejection tool 180 by a pin 192. The lever 191 is also connected to the platen 102 by a fulcrum block 193 and a pin 194. When an operator pushes down on the handle 195 of lever 191 as indicated by arrow 92, the ejection tool 180 moves upwardly as indicated by arrow 91. This results in ejection of the sealed electrode 2, as indicated by arrow 90. A spring loaded plunger 196, which is joined to the lever 191 and in contact with the bottom surface 106 of the platen 102, provides a force on the lever 191 to return it to its home position.

It is to be understood that while the present invention has been described in terms of "upper" and "lower" surfaces, and with the heater assembly located "above" the electrode holding fixture, there is no requirement that the apparatus be oriented and operated as shown with respect to gravity. These terms are simply used to indicate locations of certain elements with respect to each other and the appended drawings, and are not intended to be limiting with regard to the overall construction of the apparatus and its use.

It is, therefore, apparent that there has been provided, in accordance with the present invention, an apparatus and method for thermal encapsulation of a battery or capacitor electrode within a protective polymer film. While this invention has been described in conjunction with preferred embodiments thereof, it is evident that many alternatives, modifications, and variations will be apparent to those skilled in the art. Accordingly, the present invention is intended to embrace all such alternatives, modifications and variations that fall within the broad scope of the appended claims.

What is claimed is:

1. An apparatus for sealing a sheet of heat sealable material around a workpiece, the apparatus comprising:
   a) a workpiece holding fixture, which comprises:
      i) a platen having an upper surface and a lower surface;
      ii) a workpiece holding die disposed on the upper surface of the platen and including a deformable body comprising a pocket shaped to correspond to the perimeter of the workpiece;
      iii) a workpiece support disposed in a lower portion of the pocket of the deformable body; and
      iv) an ejection tool comprising a piston disposed in a cavity in the workpiece support and a shaft connected to the piston and passing through a hole in the workpiece support;
   b) a heater assembly, which comprises:
      i) inner and outer hold-down plates forming a heater channel there between; and
      ii) a heating element including an upper portion disposed in the heater channel and a cutting edge extending beyond the inner and outer hold-down plates, wherein a portion of the heating element is shaped to match a corresponding portion of the pocket of the deformable body; and
   c) wherein when the heater assembly and the workpiece holding fixture are moved together with the workpiece disposed in the pocket of the deformable body having a sheet of heat sealable material laying against a lower workpiece surface, an intermediate workpiece sidewall and an upper workpiece surface, the cutting edge of the heater element cuts overlapping layers of the heat sealable material against the upper surface of the deformable body.

2. The apparatus of claim 1 wherein the heating element further comprises a shoulder that serves to seal the overlapping layers of heat sealable material adjacent to the cutting edge.

3. The apparatus of claim 1 wherein the inner and outer hold-down plates are of a machinable ceramic.

4. The apparatus of claim 1 wherein the inner and outer hold-down plates are secured to a base plate.

5. The apparatus of claim 4 further comprising a tensioning block mounted on the lower surface of the base plate, wherein when the heater assembly and workpiece holding fixture are pressed together, the deformable body and the tensioning block pinch and apply tension to the intermediate sheet of heat sealable material wrapped around the workpiece.

6. The apparatus of claim 4 wherein the base plate is ceramic.

7. The apparatus of claim 1 wherein the workpiece holding die is further comprised of a base plate joined to the platen.

8. The apparatus of claim 1 wherein the workpiece support is made of a dielectric material.

9. The apparatus of claim 1 wherein the workpiece support is shaped to correspond to the perimeter of the workpiece.

10. The apparatus of claim 1 wherein the workpiece support is movable within the pocket of the deformable body, and wherein when the workpiece is enveloped in the sheet of heat sealable material disposed in the pocket of the deformable body, the workpiece support is movable against the enveloped heat sealable material by at least one spring in contact with the lower surface of the workpiece support.

11. The apparatus of claim 1 wherein the deformable body of the workpiece holding die is made of an elastic material.

12. The apparatus of claim 1 wherein the deformable body of the workpiece holding die is made of a polysiloxane elastomer.

13. The apparatus of claim 1 wherein the deformable body of the workpiece holding die includes a clearance notch that receives a wire contact extending from the workpiece.

14. The apparatus of claim 13 wherein the heating element includes a tab configured to fit in a portion of the clearance notch.

15. The apparatus of claim 1 wherein the heating element includes first and second electrical terminals provided adjacent to opposed ends thereof.

16. The apparatus of claim 15 wherein the heating element includes a third electrical terminal located between the opposed ends thereof.

17. The apparatus of claim 1 wherein a temperature of the heating element is controlled by a thermocouple.

18. The apparatus of claim 1 wherein a friction-reducing film is disposed on the upper surface of the body.

19. The apparatus of claim 18 wherein the friction-reducing film is a polyimide.

20. The apparatus of claim 1 wherein the workpiece holding fixture further comprises a tool for immobilizing the proximal ends of the folded over sheet of heat sealable material.

21. The apparatus of claim 1 wherein the workpiece holding fixture is joined to a mounting base.

22. The apparatus of claim 21 wherein the workpiece holding fixture is separated from the mounting base by a plurality of standoffs.

23. The apparatus of claim 1 wherein the workpiece holding fixture is mounted on a slide assembly.

24. The apparatus of claim 1 wherein the heater assembly is joined to a suspension plate.

25. The apparatus of claim 24 wherein the heater assembly is separated from the suspension plate by a plurality of standoffs.

26. An apparatus for sealing a sheet of heat sealable material around a workpiece, the apparatus comprising:
   a) a workpiece holding fixture, which comprises:
      i) a platen having an upper surface and a lower surface;
      ii) a workpiece holding die disposed on the upper surface of the platen and including a deformable body comprising a pocket shaped to correspond to the perimeter of the workpiece; and
      iii) a workpiece support disposed in a lower portion of the pocket of the deformable body;
   b) a heater assembly, which comprises:
      i) inner and outer hold-down plates forming a heater channel there between; and
      ii) a heating element including an upper portion disposed in the heater channel and a cutting edge extending beyond the inner and outer hold-down plates, wherein a portion of the heating element is shaped to match a corresponding portion of the pocket of the deformable body;
   c) a tensioning block; and
   d) wherein when the heater assembly and the workpiece holding fixture are moved together with the workpiece disposed in the pocket of the deformable body having a sheet of heat sealable material laying against a lower workpiece surface, an intermediate workpiece sidewall and an upper workpiece surface, the deformable body and the tensioning block pinch and apply tension to the intermediate sheet of heat sealable material wrapped around the workpiece while the cutting edge of the heater element cuts overlapping layers of the heat sealable material against the upper surface of the deformable body.

27. The apparatus of claim 26 further comprising an ejection tool comprising a piston disposed in a cavity in the workpiece support and a shaft connected to the piston and passing through a hole in the workpiece support.

28. The apparatus of claim 26 wherein the heating element further comprises a shoulder that serves to seal the overlapping layers of heat sealable material adjacent to the cutting edge.

29. The apparatus of claim 26 wherein the inner and outer hold-down plates are of a machinable ceramic secured to a ceramic base plate.

30. The apparatus of claim 26 wherein the workpiece support is made of a dielectric material.

31. An apparatus for sealing a sheet of heat sealable material around a workpiece, the apparatus comprising:
   a) a workpiece holding fixture, which comprises:
      i) a platen having an upper surface and a lower surface;
      ii) a workpiece holding die disposed on the upper surface of the platen and including a deformable body comprising a pocket shaped to correspond to the perimeter of the workpiece; and
      iii) a workpiece support disposed in a lower portion of the pocket of the deformable body;
   b) a heater assembly, which comprises:
      i) inner and outer hold-down plates forming a heater channel there between; and
      ii) a heating element including an upper portion disposed in the heater channel and a cutting edge extending beyond the inner and outer hold-down plates, wherein the heating element includes first and second electrical terminals provided adjacent to opposed ends thereof and an intermediate electrical terminal located between the first and second electrical terminals and wherein a portion of the heating element is shaped to match a corresponding portion of the pocket of the deformable body; and
   c) wherein when the heater assembly and the workpiece holding fixture are moved together with the workpiece disposed in the pocket of the deformable body having a sheet of heat sealable material laying against a lower workpiece surface, an intermediate workpiece sidewall and an upper workpiece surface, the cutting edge of the heater element cuts overlapping layers of the heat sealable material against the upper surface of the deformable body.

* * * * *